United States Patent [19]

Jeanneret nee Aab

[11] Patent Number: 4,685,905
[45] Date of Patent: Aug. 11, 1987

[54] IMPLANTABLE ARTERIAL CATHETER, ESPECIALLY MULTIDOSE INJECTION CATHETER

[75] Inventor: Hedwig Jeanneret nee Aab, La Chaux-de-Fonds, Switzerland

[73] Assignee: Clinical Plastic Products, La Chaux-de-Fonds, Switzerland

[21] Appl. No.: 865,051

[22] Filed: May 19, 1986

[30] Foreign Application Priority Data

Feb. 20, 1986 [DE] Fed. Rep. of Germany ....... 3605460

[51] Int. Cl.⁴ .......................................... A61M 5/005
[52] U.S. Cl. .................................. 604/247; 604/131
[58] Field of Search ............... 604/246, 247, 131, 132, 604/93, 27, 29, 30, 34, 48, 891, 181, 283, 280

[56] References Cited

U.S. PATENT DOCUMENTS

| | | | |
|---|---|---|---|
| 3,525,357 | 8/1970 | Koreski | 604/247 |
| 3,527,226 | 9/1970 | Hakim | 604/247 |
| 3,566,875 | 3/1971 | Stoem | 604/247 |
| 4,240,434 | 12/1980 | Newkirk | 604/247 |
| 4,360,019 | 11/1982 | Portner et al. | 604/891 |
| 4,387,879 | 6/1983 | Tauschinski | 604/247 |
| 4,457,752 | 7/1984 | Vadasz | 604/891 |
| 4,475,898 | 10/1984 | Brodner et al. | 604/247 |
| 4,544,371 | 10/1985 | Dormandy, Jr. et al. | 604/891 |
| 4,596,575 | 6/1986 | Rosenberg | 604/891 |

FOREIGN PATENT DOCUMENTS 1042754 9/1983 U.S.S.R. ............................ 604/280

OTHER PUBLICATIONS

USCI catalogue, 1974, pp. 7 and 9.

Primary Examiner—C. Fred Rosenbaum
Assistant Examiner—Gene B. Kartchner
Attorney, Agent, or Firm—Erwin S. Teltscher

[57] ABSTRACT

An implantable arterial catheter, especially a multidose catheter, comprises a multidose injection receptacle that includes a shell which bounds a chamber having an open end and has a fastening flange. A pierceable diaphragm spans the open end of the chamber to sealingly separate the chamber from the exterior of the shell. An elongated catheter tube has one end connected to the multidose injection receptacle and communicating with its chamber, and another end portion remote from the multidose injection receptacle. A safety valve is secured to the other end portion of the catheter tube and includes a conical tip component disposed at the other end portion of the catheter tube and having a flow orifice at the apex thereof, and a protective cap component surrounding the conical tip component and the other end portion of the catheter tube, secured to the catheter tube, and having a free end provided with an additional flow orifice.

5 Claims, 4 Drawing Figures

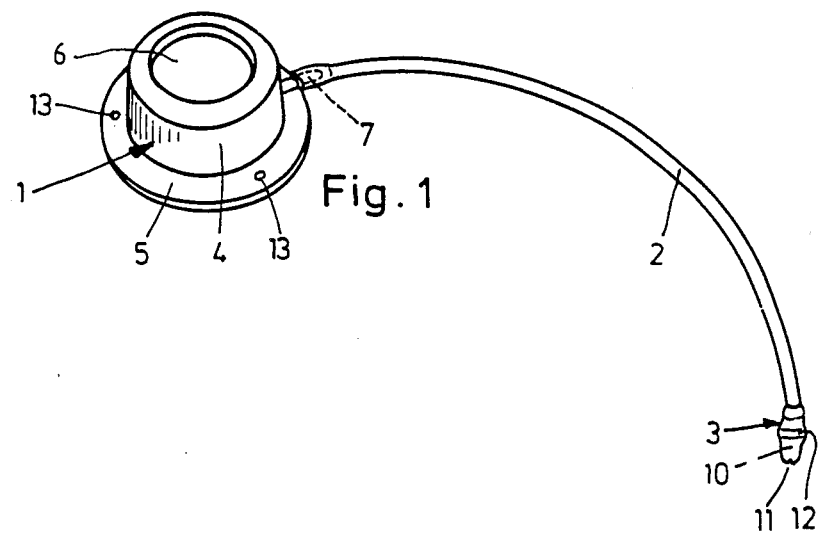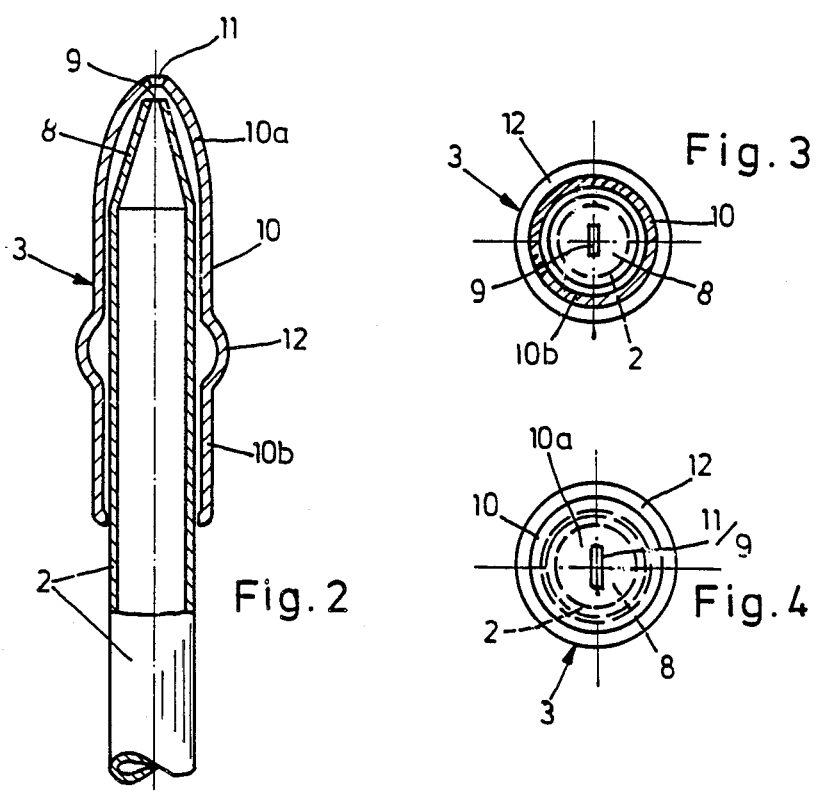

1

IMPLANTABLE ARTERIAL CATHETER, ESPECIALLY MULTIDOSE INJECTION CATHETER

BACKGROUND OF THE INVENTION

The present invention relates to catheters in general, and more particularly to implantable arterial catheters, especially multidose injection catheters.

There are already known various constructions of catheters, among them such which include a multidose injection receptacle which has a shell that bounds a chamber with an open end and is provided with a fastening flange, and a pierceable diaphragm which spans and seals the open end of the chamber and thus separates the chamber from the exterior of the multidose injection receptacle. A catheter tube has one end portion which is connected to the multidose injection receptacle and communicates with the chamber, and another end which is remote from the multidose injection receptacle and carries a safety valve.

In a typical construction of the catheter of the above type, the safety valve is constituted by the other end portion of the catheter tube which is closed and is provided with lateral flow orifices, and a protective cap which is slid onto this other end portion of the catheter tube. In this catheter construction, the pressure of the fluid being administered to the catheter recipient through the chamber of the injection receptacle and through the catheter tube expands the protective cap at the region of the lateral flow orifices of the other end portion of the catheter tube and, in this manner, the fluid can flow out of the safety valve and into the bloodstream of the recipient. Experience with safety valves of this type has shown, however, that they leave much to be desired in terms of reliability and especially prevention of return flow of fluid into the safety valve or even into the catheter tube, with attendant clogging and other problems.

SUMMARY OF THE INVENTION

Accordingly, it is a general object of the present invention to avoid the disadvantages of the prior art.

More particularly, it is an object of the present invention to provide an implantable arterial catheter which does not possess the drawbacks of the known catheters of this type.

It is still another object of the present invention to construct the catheter of the type here under consideration in such a manner as to improve its functioning and operational reliability as compared to the known catheters.

Yet another object of the present invention is to develop a catheter of the above type which allows for an easy flow of the fluid being administered into the recipient's bloodstream, while also preventing return flow into the catheter tube.

A concomitant object of the present invention is to design the catheter in such a manner as to be relatively simple, inexpensive to manufacture, easy to use, and yet reliable.

In keeping with these objects and others which will become apparent hereafter, one feature of the present invention resides in an implantable arterial catheter, especially a multidose catheter, which comprises a multidose injection receptacle including a shell which bounds a chamber having an open end, and an output port communicating with the chamber, and includes a fastening flange, and a pierceable diaphragm spanning the open end of the chamber to sealingly separate the same from the exterior of the shell; an elongated catheter tube having one end connected to the multidose injection receptacle and communicating with the chamber through the outlet port, and another end portion remote from the multidose injection receptacle; and a safety valve secured to the other end portion of the catheter tube and including a conical tip component disposed at the other end portion of the catheter tube and having a flow orifice at the apex thereof, and a protective cap component surrounding the conical tip component and the other end portion of the catheter tube, secured to the catheter tube, and having a free end provided with an additional flow orifice.

According to a preferred aspect of the present invention, the two flow orifices which are arranged coaxially downstream of one another as considered in the longitudinal direction of the catheter tube in the conical tip component, on the one hand, and in the protective cap component, on the other hand, are constituted by respective slots. The conical tip component, which is preferably made of a synthetic plastic material that is more yieldable than a synthetic plastic material of the protective cap component, can be separate from the catheter tube and be secured to such a tube by glueing, vulcanization or the like. However, the conical tip component may also be constituted as an integral part of the catheter tube.

Advantageously, the conical tip component and the protective cap component have respective wall portions which bound the respective flow orifices and sealingly contact one another in the absence of a positive pressure differential between the interior and the exterior of the respective components and yield to open the respective orifices in the presence of such positive pressure differential. It is particularly advantageous when the respective flow orifices which are bounded by these wall portions are slots.

According to another advantageous aspect of the present invention, the protective cap component has a free end region which surrounds the conical tip component with a spacing therefrom and has the additional flow orifice. This free end region of the protective cap component advantageously has a paraboloidal configuration. It is further advantageous when the additional flow orifice of the protective cap component is arranged downstream of and at a distance from the flow orifice of the conical tip component as considered in the longitudinal direction of the catheter tube.

It is also advantageous when the protective cap component has a cylindrical jacket region which surrounds the other end portion of the catheter tube and is secured thereto and when the protective cap component is provided at the jacket region thereof with a circumferentially extending outwardly projecting fixation bulge.

Thus, it may be seen that the implantable catheter disclosed here is provided, according to the present invention, with a safety valve which, on the one hand, provides for a good outflow of the fluid to be administered through the safety valve into the recipient's blood vessel and, on the other hand, efficiently prevents return flow of the blood or the like into the safety valve, thereby averting possible thrombotic clogging.

This safety valve is constituted by a conical tip component arranged at the other end portion of the catheter tube and provided with the flow orifice at its apex, and the protective cap component which overlaps and surrounds the conical tip component and the end portion of the catheter tube adjoining the conical tip component. The protective cap component is provided with the other flow orifice at its free end, so that the two flow orifices are situated behind or downstream of one another as considered in the longitudinal direction of the catheter tube. The two flow orifices are opened and closed in dependence on the pressure prevailing in the catheter tube, in that the pressure of the fluid being administered through the catheter tube opens the flow orifices in succession and with a time delay between the two openings, so that the fluid first passes from the conical tip component into the enterior of the protective cap component and then opens the other flow orifice in the protective cap component due to its increased pressure. Consequently, the fluid emerges from the safety valve, for all intents and purposes, in two successive stages.

When the pressure of the fluid being administered drops below a predetermined level, the flow orifice in the conical tip component closes immediately, and the other orifice in the protective cap component closes immediately thereafter, as a result of which there is obtained a double action in the prevention of return flow and, in this manner, any return flow of blood or other body fluids into the safety valve is avoided.

The safety valve constructed in accordance with the present invention has a simple construction and exhibits a long useful life, while also being very reliable in operation.

BRIEF DESCRIPTION OF THE DRAWING

The present invention will be described in more detail below in conjunction with the accompanying drawing, in FIG. 1 is a perspective view of an implantable arterial catheter device embodying the present invention;

FIG. 2 is a longitudinal sectional view of a safety valve arranged at one end of a catheter tube of the device of FIG. 1;

FIG. 3 is a partially cross-sectioned end elevational view of the safety valve of FIG. 2; and FIG. 4 is an end elevational view of the safety valve of FIG. 2.

DETAILED DESCRIPTION OF THE PREFERRED EMBODIMENT

Referring now to the drawing in detail, and first to FIG. 1 thereof, it may be seen that it depicts an implantable arterial catheter, especially a multidose injection catheter. Catheters of this type are used for introducing fluids, such as medication, transfusion blood, nourishment or the like, into a recipient's body over an extended period of time, either continuously or on an intermittent bases, that is, in multiple successive doses. The implantation of such catheters avoids the need for repetitively puncturing the patient's skin and blood vessel, at least once for each dose or treatment. These catheters are implanted, that is, invasively connected to the recipient's body, and the fluid to be administered is injected into the catheter as needed.

The illustrated catheter includes a multidose injection receptacle 1, to which there is connected a catheter tube 2 which carries a safety valve 3 at its end portion that is remote from the receptacle 1. The multidose injection receptacle or port 1 comprises a shell 4 which is provided at its bottom region with an outwardly projecting fastening flange 5 and which has an opening at its top region. A pierceable diaphragm 6 spans and sealingly closes the opening of the shell 4. In use, the multidose injection receptacle 1 is connected to the fascia of the recipient's body by surgical sutures passing through apertures 13 provided in a known manner in the fastening flange 5 so that the position of the catheter on the recipient's body is fixed. The catheter tube 2 has two longitudinally spaced end portions, one of which is secured to a lateral nozzle 7 of the multidose injection receptacle 1, while the other end carries the safety valve 3.

As can be seen particularly clearly in FIG. 2 of the drawing, the safety valve 3 includes a conical tip component 8 which is situated at the aforementioned other end portion of the catheter tube 2 and has a flow orifice 9 at its apex, and a protective cap component 10 which overlaps and surrounds the conical tip component 8 and a section of the other end portions of the catheter tube 2 and is secured in position on the catheter tube 2. The protective cap component 10 is also provided, at its free end, with a flow orifice 11.

The two flow orifices 9 and 11, which are arranged coaxially behind one another as considered in the longitudinal direction of the catheter tube 2 are constituted in the illustrated construction by respective slots which are automatically open or closed in dependence on the pressure of the fluid supplied to the safety valve 3 through the catheter tube 2 for introduction into the recipient's bloodstream.

The protective cap component 10 is slid onto the conical tip component 8 of the other end portion of the catheter tube 2 and is secured to the catheter tube 2 in any known manner. The protective cap component 10 is closed at its free end, except for the presence of the aforementioned slot-shaped flow orifice 11 thereat. In the illustrated construction, the protective cap component 10 has a paraboloidal shape, which essentially corresponds to the rounded head shape of a projectile, at the region of the conical tip component 8. Next to this paraboloidal formation or protective cap head 10a, the protective cap component 10 further includes a cylindrical protective cap jacket 10b which extends over and around a certain length of the other end portion of the catheter tube 2. The protective cap jacket 10b is provided with an outwardly arching fixation bulge 12 which serves for securing or fixation of the catheter tube 2 inclusive of its safety valve 3 in a blood vessel, that is, in an artery or a vein, of the recipient.

The paraboloidal protective cap head 10a surrounds and overlaps the conical tip component 8 of the catheter tube 2 with a certain spacing therefrom, and the two slot-shaped flow orifices 9 and 11 are situated substantially coaxially with one another and at a small distance downstream from each other in the longitudinal direction of the catheter tube 2.

The conical tip component 8 can be constructed as a separate part which is connected to the other end portion of the catheter tube 2. Such a connection can be obtained, for example, by glueing or by vulcanization. There further exists the possibility of making the conical tip component 8 of one piece with the remainder of the catheter tube 2. The conical tip component 8 is made of a material which is softer or more flexible than that of the protective cap component 10.

The multidose injection receptacle 1 and the catheter tube 2, as well as the safety valve 3, are made of suitable synthetic plastic materials.

During the use of the catheter, fluid which is introduced, especially injected, into the interior of the multidose injection receptacle 1 flows through the interior of the catheter tube 2 until it reaches the safety valve 3 and exits through the same into the affected blood vessel to enter the recipient's bloodstream. At this time, the pressure of the so introduced fluid opens the previously closed flow orifice 9 provided in the conical tip component 8, so that the fluid is able to enter the interior of the protective cap component 10 at the region of the conical tip component 8. Subsequently, after a time delay interval during which pressure of the fluid builds up in the spacing between the conical tip component 8 and the paraboloidal protective cap head 10a, the thus built-up pressure opens the previously closed flow orifice 11 of the protective head 10 and the fluid exits into the blood vessel. On the other hand, when the pressure of the introduced fluid decreases, the flow orifices 9 and 11 are automatically closed and, in this manner, return flow of blood or other liquid into the catheter tube 10 or even into the safety valve 3 is safely prevented.

Thus, it will be appreciated that, as a result of the construction of the safety valve 3 with two flow orifices arranged downstream of one another as considered in the direction of flow of the fluid being administered, there is obtained in dependence on the pressure of the fluid being administered either a time-delayed opening of the two orifices and, as a result of this sequential opening, a good flow of the fluid being administered through such flow orifices, or a safe (double) return flow prevention effect when the pressure of the fluid being administered is below a certain predetermined level.

While the present invention has been described and illustrated herein as embodied in a specific construction of a catheter, it is not limited to the details of this particular construction, since various modifications and structural changes are possible and contemplated by the present invention. Thus, the scope of the present invention is to be determined exclusively by the appended claims.

What is claimed is:

1. An implantable arterial catheter, especially a multidose catheter, comprising in combination
   a multidose injection receptacle including
      a shell which bounds a chamber having an open end, and having an outlet port extending laterally from said shell and communicating with said chamber, said shell including an outwardly projecting fastening flange,
      a piercable diaphragm spanning said open end of said chamber to sealingly separate the same from the exterior of the shell,
   an elongated catheter tube having one end portion connected to said multidose infjection receptacle and communicating with said chamber through said laterally extending outlet port, and having another end portion remote from said multidose injection receptacle; and
   a safety valve secured to said other end portion of said catheter tube and including
      an elongated conical tip component of a prearranged diameter disposed at said other end portion of said catheter tube, extending along a direction similar to that of said catheter tube, and having a flow orifice at an apex thereof,
      a one-piece protective cap component of a predetermined diameter, and of paraboloidal shape surrounding said conical tip component and said other end portion of said catheter tube, being secured to said catheter tube, and having a free end provided with an additional flow orifice, said flow orifices extending coaxially along the aforesaid direction at a relatively small spacing from each other,
   said conical tip component and said protective cap component having respective wall portions which bound the respective flow orifices and sealingly contact one another in the absence of a positive fluid pressure differential between the interior and the exterior of the respective component resulting from fluid passing from said outlet port through said catheter tube, but yielding to open the respective orifices sequentially so that the orifices form respective slot-like configurations in the presence of such positive pressure differential, while having a safe double return flow prevention effect when an administered fluid pressure is below a certain predetermined level, the so formed slots extending along said predetermined and prearranged diameters, but having lengths smaller than respective of said predetermined and prearranged diameters,
   said protective cap component being slid onto and secured to said conical tip component, and including a paraboloidal cap head and a protective cap jacket formed with an outwardly arching, and peripherally extending fixation bulge, said protective cap jacket being adjacent to said paraboloidal cap head,
   said conical tip component being formed of a material more yieldable than that of said protective cap component.

2. The catheter as defined in claim 1, wherein said conical tip component is glued to said catheter tube.

3. The catheter as defined in claim 1, wherein said conical tip component is vulcanized to said catheter tube.

4. The catheter as defined in claim 1, wherein said conical tip component is of one piece with said catheter tube.

5. The catheter as defined in claim 1, wherein said conical tip component and said protective cap component are made of respective synthetic plastic materials.

* * * * *